(12) United States Patent
Zhao et al.

(10) Patent No.: US 10,588,597 B2
(45) Date of Patent: Mar. 17, 2020

(54) SYSTEMS AND METHODS FOR INTERVENTIONAL PROCEDURE PLANNING

(71) Applicant: Intuitive Surgical Operations, Inc., Sunnyvale, CA (US)

(72) Inventors: Tao Zhao, Sunnyvale, CA (US); Dorin Panescu, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 971 days.

(21) Appl. No.: 14/144,186

(22) Filed: Dec. 30, 2013

(65) Prior Publication Data

US 2014/0187949 A1    Jul. 3, 2014

Related U.S. Application Data

(60) Provisional application No. 61/747,920, filed on Dec. 31, 2012.

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/085* (2013.01); *A61B 8/0841* (2013.01);
(Continued)

(58) Field of Classification Search
CPC ........... A61B 34/10; A61B 34/20; A61B 5/00; A61B 5/065
See application file for complete search history.

(56) References Cited

U.S. PATENT DOCUMENTS 6,380,732 B1    4/2002  Gilboa
6,389,187 B1    5/2002  Greenaway et al.
(Continued)

FOREIGN PATENT DOCUMENTS

CN       1925787 A      3/2007
CN     101375805 A      3/2009
(Continued)

OTHER PUBLICATIONS

International Search Report and Written Opinion for Application No. PCT/US13/78497, dated Apr. 28, 2014, 14 pages.
(Continued)

*Primary Examiner* — Baisakhi Roy
*Assistant Examiner* — Jason M Ip
(74) *Attorney, Agent, or Firm* — Haynes and Boone, LLP

(57) ABSTRACT

A method includes registering a distal segment of a guide catheter with a patient coordinate system; tracking a position of the distal segment; determining an insertion length based on the tracked position, wherein the imaging probe is disposed within the guide catheter; receiving an image of an anatomic structure from the imaging probe, the image having an image frame of reference, the distal segment having a catheter frame of reference; receiving location data associated with a target structure identified in the image, wherein the received location data is in the image frame of reference; and transforming the location data from the image frame of reference to the catheter frame of reference based on the determined insertion length and the tracked position of the distal segment, wherein transforming the location data further includes determining a roll angle for the image frame of reference with respect to the catheter frame of reference.

27 Claims, 9 Drawing Sheets

(51) Int. Cl.
| | |
|---|---|
| *A61B 34/10* | (2016.01) |
| *A61B 5/06* | (2006.01) |
| *A61B 5/00* | (2006.01) |
| *A61B 8/08* | (2006.01) |
| *A61B 10/04* | (2006.01) |
| *A61B 17/00* | (2006.01) |
| *A61B 90/00* | (2016.01) |
| *A61B 34/20* | (2016.01) |

(52) U.S. Cl.
CPC ............ *A61B 8/4263* (2013.01); *A61B 10/04* (2013.01); *A61B 17/00234* (2013.01); *A61B 34/10* (2016.02); *A61B 5/0066* (2013.01); *A61B 5/065* (2013.01); *A61B 8/4245* (2013.01); *A61B 2034/102* (2016.02); *A61B 2034/107* (2016.02); *A61B 2034/2051* (2016.02); *A61B 2090/364* (2016.02)

(56) References Cited

U.S. PATENT DOCUMENTS

| | | |
|---|---|---|
| 6,468,265 B1 | 10/2002 | Evans et al. |
| 7,206,462 B1 | 4/2007 | Betke et al. |
| 7,506,650 B2 | 3/2009 | Lowe et al. |
| 7,725,214 B2 | 5/2010 | Diolaiti |
| 7,772,541 B2 | 8/2010 | Froggatt et al. |
| 7,781,724 B2 | 8/2010 | Childers et al. |
| 7,930,065 B2 | 4/2011 | Larkin et al. |
| 8,062,212 B2 | 11/2011 | Belson |
| 8,226,546 B2 | 7/2012 | Belson |
| 8,248,414 B2 | 8/2012 | Gattani et al. |
| 8,303,505 B2 | 11/2012 | Webler et al. |
| 8,317,746 B2 | 11/2012 | Sewell et al. |
| 8,361,090 B2 | 1/2013 | Belson |
| 8,398,541 B2 | 3/2013 | Dimaio et al. |
| 8,517,923 B2 | 8/2013 | Belson et al. |
| 8,611,983 B2 | 12/2013 | Glossop et al. |
| 2002/0115941 A1 | 8/2002 | Whayne et al. |
| 2002/0133057 A1 | 9/2002 | Kukuk |
| 2003/0085890 A1* | 5/2003 | Baumberg ............... G06T 15/04 345/420 |
| 2003/0093067 A1 | 5/2003 | Panescu |
| 2004/0163650 A1* | 8/2004 | Lowe ....................... A61F 6/18 128/830 |
| 2004/0254458 A1* | 12/2004 | Govari ...................... A61B 8/12 600/437 |
| 2005/0182295 A1 | 8/2005 | Soper et al. |
| 2006/0013523 A1 | 1/2006 | Childlers et al. |
| 2006/0025677 A1* | 2/2006 | Verard .................. A61B 90/36 600/423 |
| 2006/0239544 A1 | 10/2006 | Yankelevitz et al. |
| 2007/0237373 A1 | 10/2007 | Kiraly et al. |
| 2007/0249911 A1 | 10/2007 | Simon |
| 2007/0293734 A1 | 12/2007 | Coste-Maniere et al. |
| 2008/0082109 A1 | 4/2008 | Moll et al. |
| 2008/0123922 A1 | 5/2008 | Gielen et al. |
| 2008/0255505 A1* | 10/2008 | Carlson ............... A61B 19/2203 604/95.04 |
| 2008/0287803 A1 | 11/2008 | Li et al. |
| 2008/0294034 A1 | 11/2008 | Krueger et al. |
| 2009/0062813 A1 | 3/2009 | Prisco et al. |
| 2009/0156895 A1 | 6/2009 | Higgins et al. |
| 2009/0163810 A1 | 6/2009 | Kanade et al. |
| 2009/0171184 A1 | 7/2009 | Jenkins et al. |
| 2009/0227861 A1 | 9/2009 | Ganatra et al. |
| 2009/0262980 A1* | 10/2009 | Markowitz .......... A61B 5/0422 382/103 |
| 2009/0268010 A1 | 10/2009 | Zhao et al. |
| 2010/0249506 A1 | 9/2010 | Prisco |
| 2011/0112569 A1 | 5/2011 | Friedman et al. |
| 2011/0207997 A1* | 8/2011 | Greenburg ............... A61B 5/05 600/104 |
| 2011/0282140 A1 | 11/2011 | Itkowitz et al. |
| 2012/0004533 A1* | 1/2012 | Peng ........................ A61B 6/12 600/424 |
| 2012/0035438 A1 | 2/2012 | Ferren et al. |
| 2012/0059378 A1 | 3/2012 | Farrell |
| 2012/0065481 A1 | 3/2012 | Hunter et al. |
| 2012/0203067 A1 | 8/2012 | Higgins et al. |
| 2012/0289777 A1 | 11/2012 | Chopra et al. |
| 2012/0289843 A1 | 11/2012 | Chopra et al. |
| 2012/0296620 A1 | 11/2012 | Aulbach |
| 2012/0327204 A1 | 12/2012 | Friedman et al. |
| 2012/0330622 A1 | 12/2012 | Butson et al. |
| 2013/0085774 A1 | 4/2013 | Chen et al. |
| 2013/0303876 A1 | 11/2013 | Gelfand et al. |
| 2014/0188440 A1 | 7/2014 | Donhowe et al. |
| 2015/0094914 A1 | 4/2015 | Abreu |
| 2015/0221105 A1 | 8/2015 | Tripathi et al. |
| 2015/0347682 A1 | 12/2015 | Chen et al. |
| 2017/0132812 A1 | 5/2017 | Tripathi et al. |

FOREIGN PATENT DOCUMENTS

| | | |
|---|---|---|
| CN | 100515332 C | 7/2009 |
| CN | 101862205 A | 10/2010 |
| CN | 102186404 A | 9/2011 |
| CN | 102481115 A | 5/2012 |
| CN | 102740755 A | 10/2012 |
| CN | 102740791 A | 10/2012 |
| EP | 1481637 A1 | 12/2004 |
| EP | 1779802 A2 | 5/2007 |
| EP | 2238901 A2 | 10/2010 |
| EP | 2377457 A1 | 10/2011 |
| JP | 2009542374 A | 12/2009 |
| JP | 2010540021 A | 12/2010 |
| JP | 2011525827 A | 9/2011 |
| WO | WO-2005082246 A1 | 9/2005 |
| WO | WO-2006124388 A1 | 11/2006 |
| WO | WO-2009023801 A1 | 2/2009 |
| WO | WO-2010049834 A1 | 5/2010 |
| WO | WO-2010078009 A1 | 7/2010 |

OTHER PUBLICATIONS

International Search Report and Written Opinion for Application No. PCT/US13/78508, dated Apr. 3, 2014, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. 13867391.8, dated Jul. 22, 2016, 7 pages.
Extended European Search Report for Application No. 13868283.6, dated Jul. 26, 2016, 7 pages.
Office Action dated Dec. 28, 2016 for Chinese Application No. 201380068398.6 filed Dec. 31, 2013, 18 pages.
Wen R., et al., "Robot-Assissted RF Ablation with Interactive Planning and Mixed Reality Guidance," IEEE/SICE International Symposium on System Integration, 2012, pp. 31-36.
Yaniv Z., et al., "Neddle-Based Interventions With the Image-Guided Surgery Toolkit (IGSTK): From Phantoms to Clinical Trials," IEEE Transactions on Biomedical Engineering, 2010, vol. 57(4), pp. 922-933.
Extended European Search Report for Application No. 18188100.4, dated Nov. 13, 2018, 8 pages.

* cited by examiner

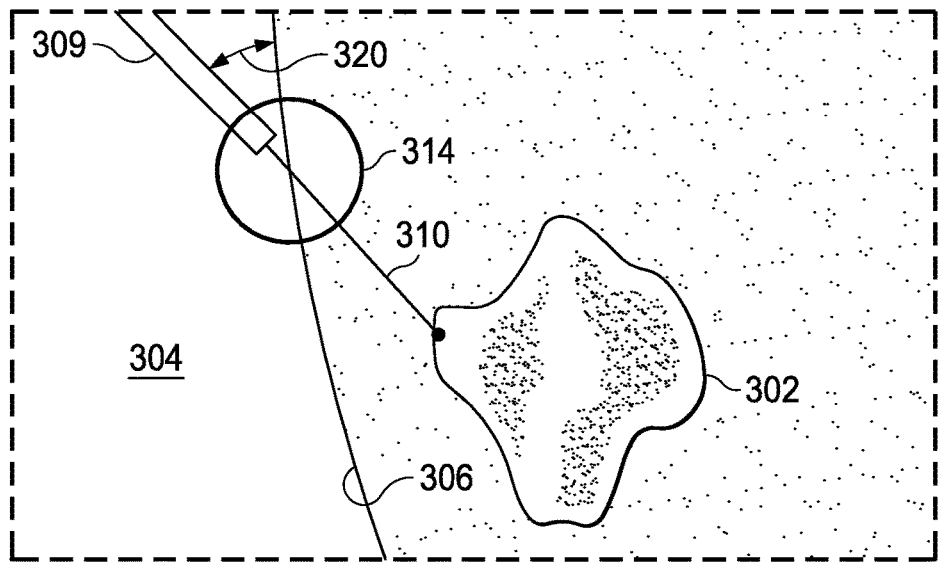
Fig. 5
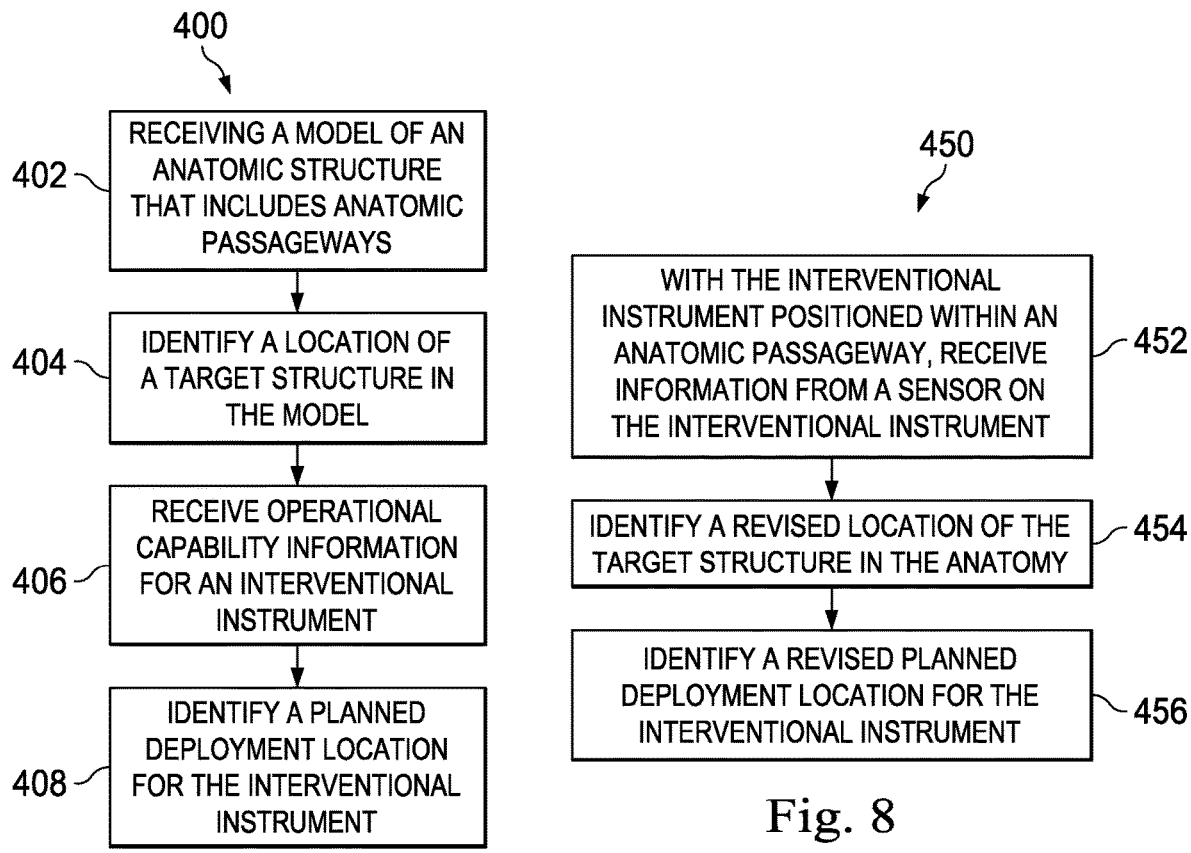
Fig. 7
Fig. 8

SYSTEMS AND METHODS FOR INTERVENTIONAL PROCEDURE PLANNING

CROSS-REFERENCE TO RELATED APPLICATIONS

This application claims the benefit of U.S. Provisional Application 61/747,920 filed Dec. 31, 2012, which is incorporated by reference herein in its entirety.

FIELD

The present disclosure is directed to systems and methods for navigating a patient anatomy to conduct a minimally invasive procedure, and more particularly to systems and methods for planning a procedure to deploy an interventional instrument.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. To assist the clinician in navigating the instrument through the passageways, models of the passageway are prepared using pre-operative or inter-operative imaging. Current systems for deploying an interventional instrument identify an instrument deployment location as the point within the modeled passageways closest to the target tissue location. This closest-point deployment location may be difficult to access given the constraints of the interventional instrument or the anatomy. Improved systems and methods are needed to determine a planned instrument deployment location for conducting a procedure on the target tissue location.

SUMMARY

The embodiments of the invention are summarized by the claims that follow the description.

In one embodiment, a method of deploying an interventional instrument is performed by a processing system. The method comprises receiving an image of an anatomic structure from an imaging probe. The image has an image frame of reference. The imaging probe is extendable distally beyond a distal end of a guide catheter. The distal end of the guide catheter has a catheter frame of reference. The method further includes receiving location data associated with a target structure identified in the image. The received location data is in the image frame of reference. The method further comprises transforming the location data associated with the target structure from the image frame of reference to the catheter frame of reference.

In another embodiment, a system comprises non-transitory computer readable media containing computer executable instructions for planning a procedure to deploy an interventional instrument. The instructions include instructions for receiving an image of an anatomic structure from an imaging probe. The image has an image frame of reference, wherein the imaging probe is extendable distally beyond a distal end of a guide catheter, the distal end of the guide catheter having a catheter frame of reference. The instructions further include instructions for receiving location data associated with a target structure identified in the image. The received location data is in the image frame of reference. The instructions further include instructions for transforming the location data associated with the target structure from the image frame of reference to the catheter frame of reference.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 5 is a view of a portion of the FIG. 4.

FIG. 7 is a flowchart describing a method for identifying a planned deployment location for an interventional instrument.

FIG. 8 is a flowchart describing a method for revising the planned deployment location based upon sensor feedback.

FIG. 10b illustrates an image generated by the imaging system of FIG. 10a.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
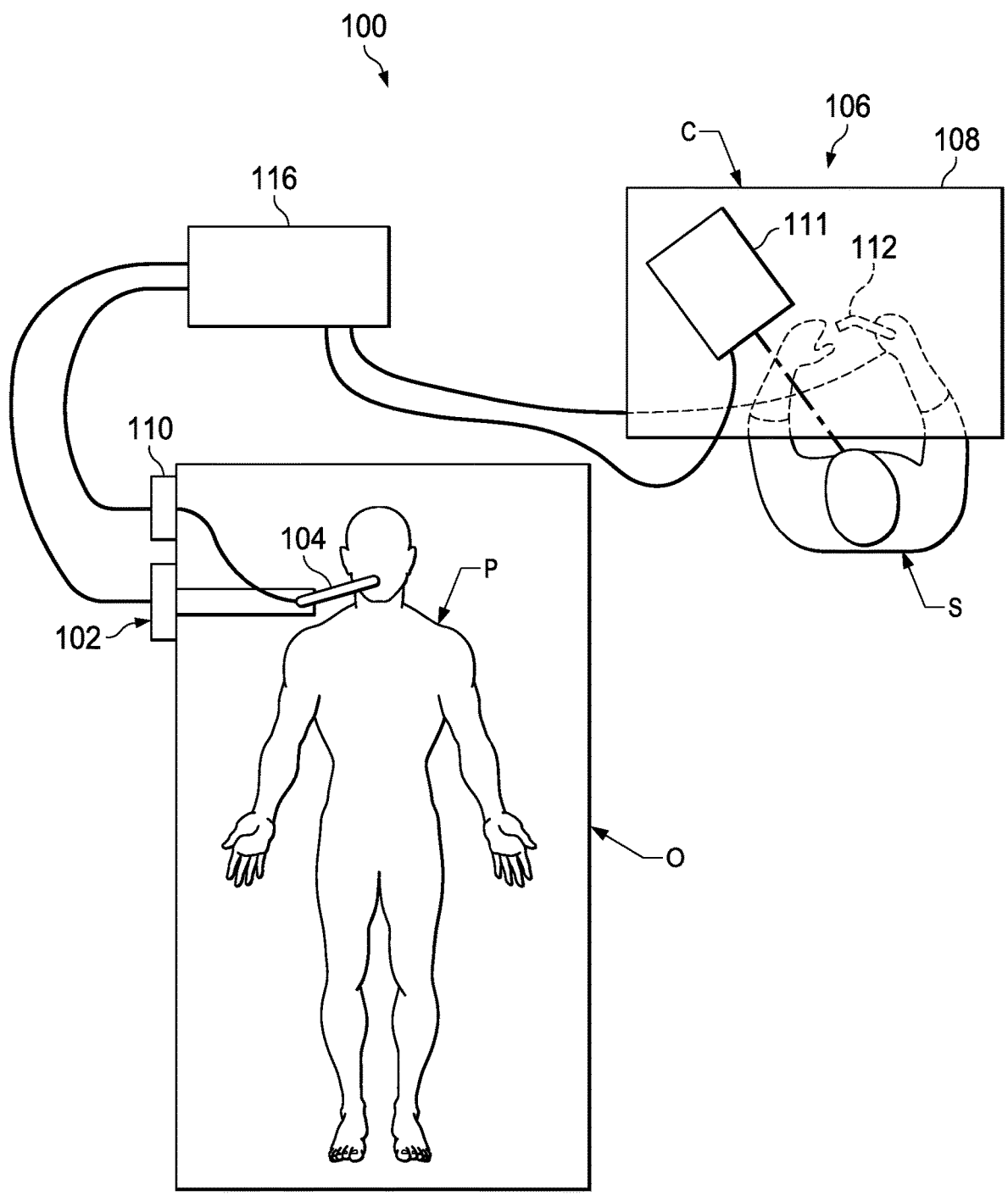
FIG. 1 is a teleoperated interventional system, in accordance with embodiments of the present disclosure.

Referring to FIG. 1 of the drawings, a teleoperated interventional system for use in, for example, surgical, diagnostic, therapeutic, or biopsy procedures, is generally indicated by the reference numeral 100. As shown in FIG. 1, the teleoperated system 100 generally includes an interventional manipulator assembly 102 for operating an interventional instrument 104 in performing various procedures on the patient P. The assembly 102 is mounted to or near an operating table O. A master assembly 106 allows the surgeon S to view the interventional site and to control the slave manipulator assembly 102.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, data gloves, trigger-guns, hand-operated controllers, voice recognition devices, body motion or presence sensors, or the like. In some embodiments, the control device(s) 112 will be provided with the same degrees of freedom as the associated interventional instruments 104 to provide the surgeon with telepresence, or the perception that the control device(s) 112 are integral with the instruments 104 so that the surgeon has a strong sense of directly controlling instruments 104. In other embodiments, the control device(s) 112 may have more or fewer degrees of freedom than the associated interventional instruments 104 and still provide the surgeon with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, or the like).

In alternative embodiments, the teleoperated system may include more than one slave manipulator assembly and/or more than one master assembly. The exact number of manipulator assemblies will depend on the interventional procedure and the space constraints within the operating room, among other factors. The master assemblies may be collocated, or they may be positioned in separate locations. Multiple master assemblies allow more than one operator to control one or more slave manipulator assemblies in various combinations.

An optional visualization system 110 may include an endoscope system such that a concurrent (real-time) image of the interventional site is provided to surgeon console C. The concurrent image may be, for example, a two- or three-dimensional image captured by an endoscopic probe positioned within the interventional site. In this embodiment, the visualization system 110 includes endoscopic components that may be integrally or removably coupled to the interventional instrument 104. In alternative embodiments, however, a separate endoscope attached to a separate manipulator assembly may be used to image the interventional site. Alternatively, a separate endoscope assembly may be directly operated by a user, without teleoperational control. The endoscope assembly may include active steering (e.g., via teleoperated steering wires) or passive steering (e.g., via guide wires or direct user guidance). The visualization system 110 may be implemented as hardware, firmware, software, or a combination thereof, which interacts with or is otherwise executed by one or more computer processors, which may include the processor(s) of a control system 116.

A display system 111 may display an image of the interventional site and interventional instruments captured by the visualization system 110. The display 111 and the master control device(s) 112 may be oriented such that the relative positions of the imaging device in the scope assembly and the interventional instruments are similar to the relative positions of the surgeon's eyes and hand(s) so the operator can manipulate the interventional instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the interventional site recorded and/or modeled preoperatively using imaging technology such as computerized tomography (CT), magnetic resonance imaging (MRI), fluoroscopy, thermography, ultrasound, optical coherence tomography (OCT), diffuse optical tomography (DOT), thermal imaging, impedance imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual visualization image in which the actual location of the interventional instrument is registered (e.g., dynamically referenced) with preoperative or concurrent images from the modeled anatomy to present the surgeon S with a virtual image of the internal interventional site at the location of the tip of the interventional instrument.

In other embodiments, the display system 111 may display a virtual visualization image in which the actual location of the interventional instrument is registered with prior images (including preoperatively recorded images) or concurrent images from the modeled anatomy to present the surgeon S with a virtual image of an interventional instrument at the interventional site. An image of a portion of the interventional instrument may be superimposed on the virtual image to assist the surgeon controlling the interventional instrument.

In FIG. 1, a control system 116 includes at least one processor (not shown), and typically a plurality of processors, for effecting control between the slave surgical manipulator assembly 102, the master assembly 106, the visualization system 110, and the display system 111. The control system 116 also includes programmed instructions (e.g., a computer-readable medium storing the instructions) to implement some or all of the methods described herein. While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed at the master assembly, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 116 supports wireless communication protocols such as Bluetooth, IrDA, HomeRF, IEEE 802.11, DECT, and Wireless Telemetry.

In some embodiments, control system 116 may include one or more servo controllers to provide force and torque feedback from the interventional instruments 104 to one or more corresponding servomotors for the control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a manipulator arm cart positioned adjacent to the patient's body.

Each manipulator assembly 102 supports a interventional instrument 104 and may comprise a kinematic structure of one or more non-servo controlled links (e.g., one or more links that may be manually positioned and locked in place, generally referred to as a set-up structure) and a teleoperated manipulator. The teleoperated manipulator assembly 102 is driven by a plurality of actuators (e.g., motors). These motors actively move the teleoperated manipulators in response to commands from the control system 116. The motors are further coupled to the interventional instrument so as to advance the interventional instrument into a naturally or surgically created anatomical orifice and to move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

Figure 2:
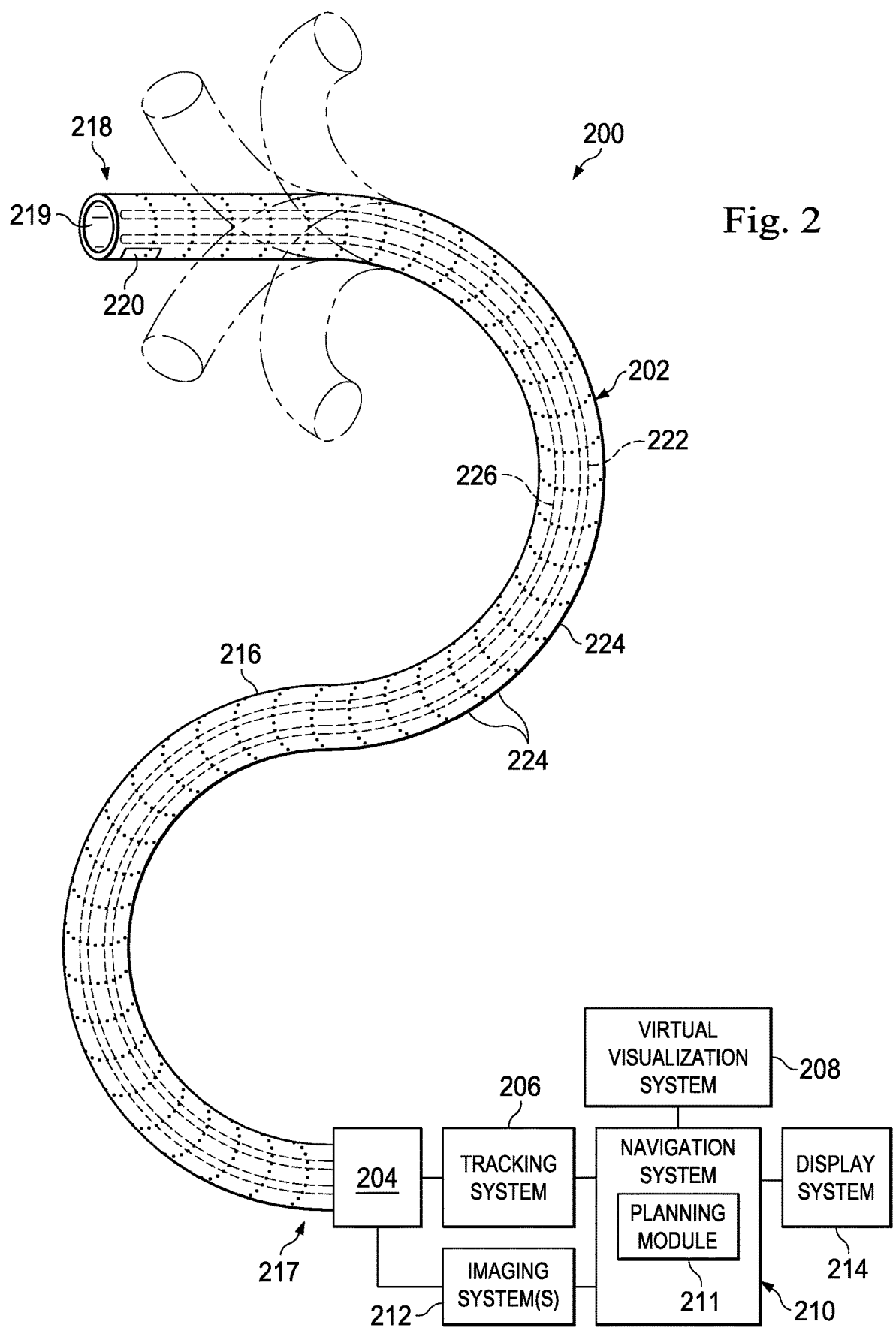
FIG. 2 illustrates an interventional instrument system utilizing aspects of the present disclosure.

FIG. 2 illustrates a minimally invasive system 200 utilizing aspects of the present disclosure. The system 200 may be incorporated into a teleoperated interventional system, such as system 100. Alternatively, the system 200 may be used for exploratory procedures or in procedures involving traditional manually operated interventional instruments, such as laparoscopic instruments. The system 200 includes a catheter system 202 (e.g., part of the instrument 104) coupled by an interface unit 204 to a tracking system 206. A navigation system 210 (e.g., part of the control system 116) processes information from a virtual visualization system 208, one or more imaging systems 212, and/or the tracking system 206 to generate one or more image displays on a display system 214 (e.g., part of the display system 111). The system 200 may further include optional operation and support systems (not shown) such as illumination systems, steering control systems, irrigation systems, and/or suction systems.

The catheter system 202 includes an elongated flexible body 216 having a proximal end 217 and a distal end 218. A channel 219 extends within the flexible body 216. In one embodiment, the flexible body 216 has an approximately 3 mm outer diameter. Other flexible body outer diameters may be larger or smaller. The catheter system 202 optionally includes a sensor system which includes a position sensor system 220 (e.g., an electromagnetic (EM) sensor system) and/or a shape sensor system 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. The position sensor system 220 and the shape sensor system 222 interface with the tracking system 206. The tracking system 206 may be implemented as hardware, firmware, software or a combination thereof which interact with or are otherwise executed by one or more computer processors, which may include the processors of a control system 116.

The position sensor system 220 may be an EM sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The shape sensor system 222 includes an optical fiber aligned with the flexible body 216 (e.g., provided within an interior channel (not shown) or mounted externally). The tracking system 206 may be coupled to a proximal end of the optical fiber. In one embodiment, the optical fiber has a diameter of approximately 200 μm. In other embodiments, the dimensions may be larger or smaller. Alternatively, external imaging of the anatomy containing the catheter can be used to reconstruct the shape of the catheter.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed by the tracking system 206 for detecting the shape of the catheter system 202 and for utilizing that information to assist in interventional procedures. The tracking system 206 may include a detection system for generating and detecting the light used for determining the shape of the catheter system 202. This information, in turn, can be used to determine other related variables, such as velocity and acceleration of the parts of an interventional instrument. The sensing may be limited only to the degrees of freedom that are actuated by the teleoperational system, or may be applied to both passive (e.g., unactuated bending of the rigid members between joints) and active (e.g., actuated movement of the instrument) degrees of freedom.

The flexible body 216 may optionally house one or more image capture probes 226 that transmit captured image data to the imaging system(s) 212. For example, the image capture probe 226 may be an endoscopic probe including a tip portion with a stereoscopic or monoscopic camera disposed near the distal end 218 of the flexible body 216 for capturing images (including video images) that are transmitted to the imaging system 212. The image capture probe 226 may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

Additionally or alternatively, the image capture probe 226 may be a sensor probe for use with a imaging technology such as ultrasound, OCT, or DOT. For example, the probe may include a transmitter and receiver arrangement, such as an ultrasound transducer. The ultrasonic transducer can be mounted at an end of an elongated shaft. Such a source can be used to obtain a preoperative or intraoperative two-dimensional or three-dimensional image, or model, of the anatomic region where the interventional procedure is to be performed. As a two-dimensional source, the ultrasonic transducer can be used to obtain a single ultrasound image. As a three-dimensional source it can be used to obtain a plurality of spaced ultrasonic images, or cuts, thereby to provide sufficient information for construction of a three-dimensional model. Accordingly, it can be arranged to move, including rotate, within an anatomic site to capture such images, or cuts. This can typically be achieved, for example, in accordance with a pre-programmed sequence for moving the ultrasound transducer by teleoperational control, manual movement of the ultrasound transducer, or the like.

The body 216 may also house cables, linkages, or other steering controls (not shown) that extend between the interface 204 and the tip distal end 218 to controllably bend or turn the distal end 218 as shown for example by the dotted line versions of the distal end. The catheter system may be steerable or, alternatively, may be non-steerable with no integrated mechanism for operator control of the instrument bending. The flexible body 216 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like.

Figure 3:
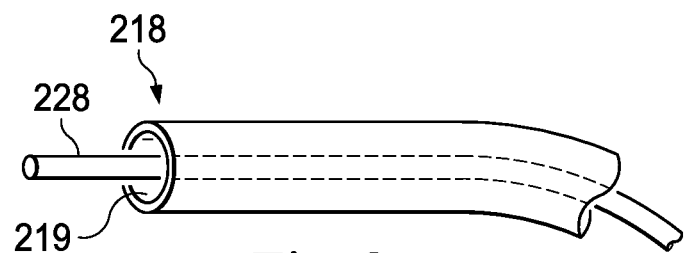
FIG. 3 illustrates a distal end of the interventional instrument system of FIG. 2 with an extended interventional tool.

As shown in greater detail in FIG. 3, interventional tool(s) 228 for such procedures as surgery, biopsy, ablation, illumination, irrigation, or suction can be deployed through the channel 219 of the flexible body 216 and used at a target location within the anatomy. The intervertebral tool 228 may also be the image capture probe. The tool 228 may be advanced from the opening of the channel 219 to perform the procedure and then retracted back into the channel when the procedure is complete. The interventional tool 228 may be removed from the proximal end 217 of the catheter flexible body or from another optional instrument port (not shown) along the flexible body.

The virtual visualization system 208 provides navigation assistance to the catheter system 202. Virtual navigation using the virtual visualization system is based upon reference to an acquired dataset associated with the three dimensional structure of the anatomical passageways. More specifically, the virtual visualization system 208 processes images of the interventional site recorded and/or modeled using imaging technology such as computerized tomography (CT), magnetic resonance imaging (MRI), fluoroscopy, thermography, ultrasound, OCT, DOT, thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor systems may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The navigation system 210, as part of the control system 116, processes information from the virtual visualization system 208, the one or more imaging systems 212, and/or the tracking system 206 to determine a navigational path for the interventional instrument through the anatomical system to the target anatomical structure. The navigation system 210 may also monitor the navigational path of the interventional instrument as it moves through the anatomical system to a target structure. The navigation system 210 includes a planning module 211 that allows a clinician to locate a target anatomical structure (e.g., a tumor) in the anatomical model prepared by the virtual visualization system 208 and to identify a navigational path through anatomical passageways to reach the target structure to perform an interventional procedure (e.g., a biopsy) with the interventional instrument. The target localization and navigational path determination may be automated such that the navigation system identifies one or more navigational paths. Alternatively, a clinician may determine the navigational path from the anatomic model and optionally communicate the selected path to the navigational system. In still another alternative, the planning module uses a hybrid automated/clinician selected navigational path determination in which the clinician may modify a system planned path or in which the clinician may enter parameters such as anatomical areas to avoid or instrument limitations that constrain the planned navigational path suggested by the planning module 212.

Figure 4:
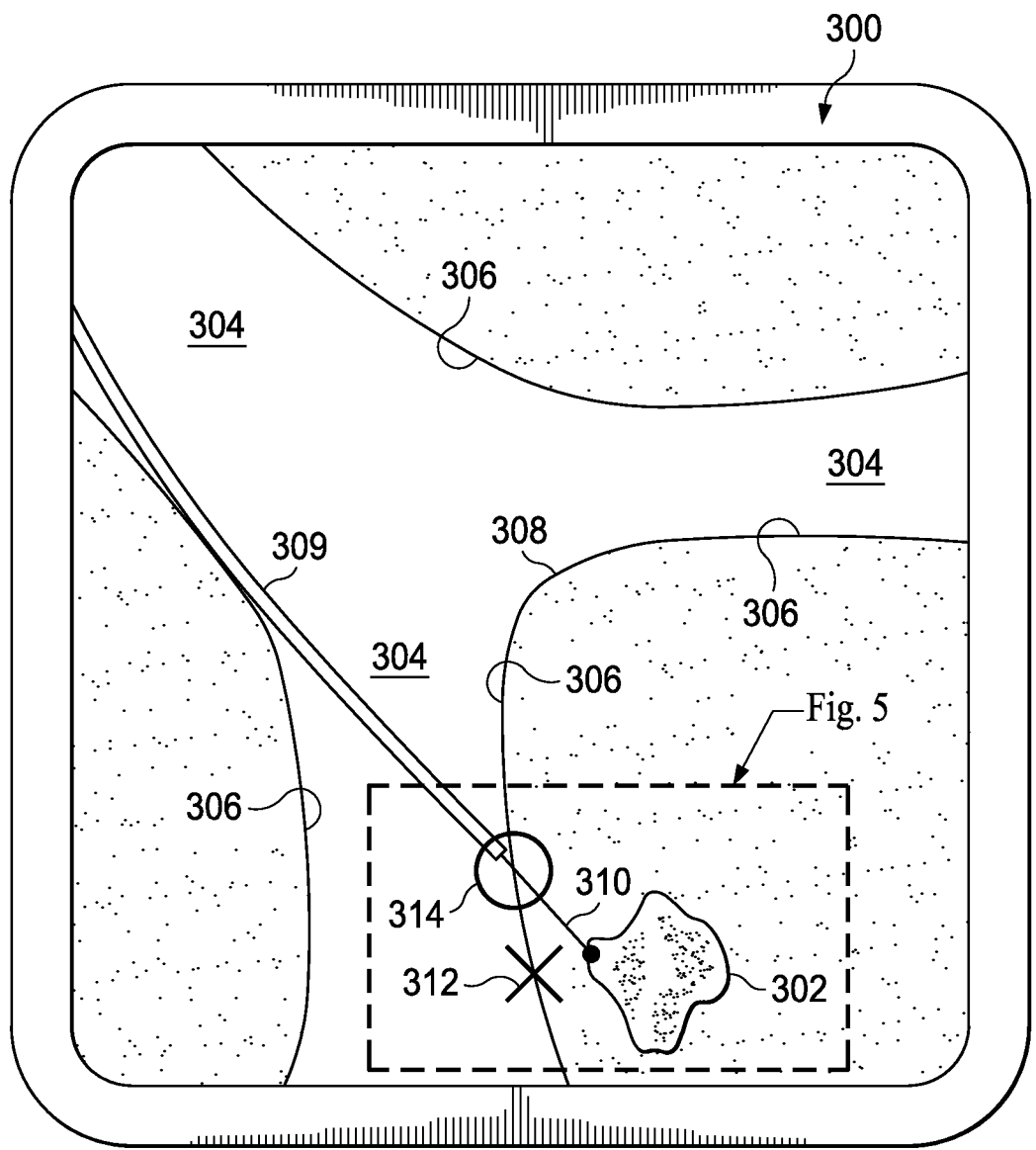
FIG. 4 illustrates an anatomic model image with a distal end of an interventional instrument at a deployment location.

The navigation planning module generates or allows the clinician to select a planned deployment location within an anatomical passageway for parking a distal end of the interventional instrument to conduct the interventional procedure. Referring now to FIG. 4, a virtual image 300 of target structure 302, such as a tumor, and nearby anatomic passageways 304 is depicted. The passageways include passageway walls 306 and carina 308. In this embodiment, the anatomic passageways are bronchial passageways of the lung, but the systems and methods of this disclosure may be suitable for use in other natural or surgically created passageways in anatomical systems such as the colon, the intestines, the kidneys, the heart, or the circulatory system. An interventional instrument with a flexible body 309 (substantially similar to flexible body 216) and an extended interventional tool 310 are shown. In one embodiment, a navigation planning module identifies the planned deployment location as a location 312 along a wall of an anatomic passageway closest to or nearby to the target structure. However, selecting the deployment location entirely on the basis of proximity to the target structure may result in a selected deployment location that is inaccessible or not easily accessible by the interventional instrument. For example, the interventional instrument may be incapable of bending sufficiently within the passageway to access the proximity based deployment location. Additionally the selected deployment location or the navigational path to the deployment location may not consider anatomical constraints, such as scar or diseased tissue to avoid. As another example, a deployment location can be selected to minimize the amount of tissue deformation and thus the risk of tissue damage.

In other embodiments, a navigation planning module selects the deployment location based upon a plurality of factors, which in some instances may be procedural characteristics, such as the distance to the target structure, and/or the position of the target structure relative to other anatomic features. In other embodiments, the navigation planning module may additionally or alternatively receive and use information about the operational capability of the interventional instrument to determine a deployment location. For example, information pertaining to the bending capability of the instrument may be considered, such as the flexibility and elasticity of the catheter material, any preformed shape characteristics of the catheter or tools passed through the channel of the catheter, the steerability of the distal end of the catheter or tool (e.g., the degree to which the distal tip of the catheter may be curved relative to the main axis of the catheter), and the curvature along the length of the catheter. Other characteristics of the interventional instrument may also be used to determine the deployment location including the diameter of the catheter, the diameter of the tool, the trajectory of the tool when extended from the catheter (e.g., curved, straight), the movement of the tool (e.g., sweeping, spinning, linear), the maximum angulation of the axis of the tool versus the axis of the catheter, the maximum length the tool can be extended from the catheter, and any anchoring structures at the distal tip of the catheter providing frictional contact with the passageway wall. The information pertaining to the bending capability and/or the information related to the characteristics of the interventional instrument are exemplary factors that can be used to determine the operational capability of the interventional instrument within the anatomical passageways.

The navigation planning module may also or alternatively receive and use information about the patient anatomy to determine a deployment location. Such information may include, for example, the location of the carinas of the anatomical passageways nearest to the target structure and the size of the passageways nearest to the target structure. Other anatomic information may include the elasticity of the anatomical passageways including the impact that any disease processes may have had on the elasticity of the passageways. The navigation planning model may also consider the surrounding anatomic tissue to, for example, select a deployment location that reduces the risk to surrounding tissue. As one example, a deployment location away from the perimeter of a lung may be selected to avoid the risk of puncturing the lung with the deployed tool. The navigation planning model may also consider the anatomy of the target structure to access a preferred location of the target structure. For example, the deployment location may be selected such that a biopsy tool avoids a calcified part of a tumor. If the shape of the target is not round, the deployment location can be selected to maximize the probability of hitting the target considering the navigation uncertainty and the shape of the target.

The navigation planning module may also consider information about the relationship between the interventional instrument and the patient anatomy such as the distance of the target structure from the end of the catheter. Referring to FIG. 5, the navigation planning module may also consider the angle of approach 320 between the interventional tool and the passageway wall. For example, an approach angle of 90° may impracticable due to the small size of the passageway and the bendability of the distal tip of the catheter. An approach angle of 1° may also be unsuitable because of the risk that the interventional tool may graze the surface of the passageway wall without penetrating. For these reasons, the navigation planning module may select a deployment location such that the approach angle is between approximately 30° and 90°.

Referring again to FIG. 4, after the navigation planning module evaluates the factors related to the interventional instrument and the patient anatomy, a deployment location 314 on the wall of an anatomic passageway is identified. Optionally, the navigation planning module may provide a suggested navigational path to the deployment location. The clinician can then direct the distal end of the interventional instrument to the deployment location. The clinician may manually control the navigation of the interventional instrument based upon virtual or real image guidance. Alternatively, the clinician can teleoperationally control the navigation of the interventional instrument or allow computer-controlled navigation of the interventional instrument along the suggested navigational path. After the distal end of the interventional instrument is positioned at the deployment location, the interventional tool is extended from the catheter, through the passageway wall and into contact with the target structure. In some circumstances, for example when a target structure is located within an anatomic passageway, the deployment location may be located within the lumen of the passageway, rather than on the wall of the passageway. For example when the target structure is within the passageway, the deployment location may be on a surface of the target structure.

FIG. 7 is a flowchart describing a method 400 used by the navigation planning module for identifying a planned deployment location for an interventional instrument. At 402, a model of an anatomic structure is received. The anatomic structure includes a plurality of anatomic passageways which are illustrated by the model. The model is formed from two or three dimensional images of the interventional site recorded and/or modeled preoperatively or interoperatively using imaging technology such as CT, MRI, fluoroscopy, thermography, ultrasound, OCT, thermal imaging, impedance imaging, laser imaging, nanotube X-ray imaging, or the like. Receipt of the model may include receiving information about the patient anatomy derived from the model, from user inputs describing the patient anatomy, or from other reference sources. Such information about the patient anatomy may include, for example, the closest location(s) within an anatomic passageway(s) to the target structure, the location of the carinas of the anatomical passageways nearest to the target structure, and the size of the passageways nearest to the target structure. Other anatomic information may include the elasticity of the anatomical passageways, the anatomy of the target structure to access a preferred location of the target structure, and the type of surrounding tissue and any risk associated with contacting the surrounding tissue.

At 404, a location of a target structure (e.g., a tumor) is identified in the model. Identifying the target structure may include determining or receiving information about the target structure from the model, from user inputs describing the target structure, or from other reference sources. Such information about the target structure may include, for example, the shape of the target structure, the one or more substances that form the target structure, and the location of the surfaces of the target structure relative to nearby anatomic passageways.

At 406, information about the operational capability of the interventional instrument is received. The information received to determine the operational capability of the interventional instrument may include, for example, information pertaining to the bending capability of the instrument such as the flexibility and elasticity of the catheter material, any preformed shape characteristics of the catheter or tools passed through the channel of the catheter, the steerability of the distal end of the catheter or tool, and the curvature along the length of the catheter. The operational capability of the interventional instrument may also be determined from characteristics of the interventional instrument such as the diameter of the catheter, the diameter of the tool, the maximum angulation of the axis of the tool versus the axis of the catheter, the maximum length the tool can be extended from the catheter, and any anchoring structures at the distal tip of the catheter providing frictional contact with the passageway wall.

At 408, a planned deployment location for the interventional instrument is located. The planned deployment location may be marked on the model of the plurality of passageways. The planned deployment location can be selected based upon the instrument operational capability information, the target structure information, the patient anatomy information, or a combination of the types of information. The selected deployment location may be at a point in an anatomic passageway nearest to the target structure. However, in many patients a nearest point deployment location may be impossible for the distal end of the interventional instrument to reach because the instrument has insufficient bend capability within the size and elasticity constraints of the selected anatomic passageway. A more suitable deployment location may be at a point on an anatomic passageway wall where the interventional instrument has an approach angle to the passageway wall that is within the bending capability of the instrument. For example, if the interventional instrument has an inflexible distal end that permits little or no bending, a suitable deployment location may be at a carina near the target structure. At the carina the interventional instrument may be deployed at an approximately 90° approach angle to the passageway wall with minimal bending of the distal end of the instrument. As another example, the navigation planning module may select a deployment location such that the approach angle is between approximately 30° and 90°. When selecting a deployment location, the planning system also confirms that the interventional tool is capable of extending from the catheter a sufficient distance to reach the target structure to perform the interventional procedure.

As described, the planned deployment location may be located based on the analysis of the instrument operational capability, the target structure, and the patient anatomy. Alternatively or in combination with the system assessment, the planned deployment location may be identified by a clinician and communicated to the navigation planning module to locate or mark the clinician-identified planned deployment location in the model. When the navigation planning module receives the clinician-identified planned deployment location, the module may compare it with the system-identified deployment location. A visual or audible feedback cue may be issued if the clinician-identified deployment location is objectionable (e.g., "The chosen biopsy needle is not long enough to reach the target from this deployment location.").

Optionally, the navigation planning module identifies multiple elective deployment locations. The elective deployment locations may be coded (e.g., with color on the display) to provide information about the relative quality of the elective deployment locations for deploying the interventional instrument to perform the procedure. A clinician may select one of elective deployment locations to be the planned deployment location. Alternatively, more than one planned deployment location may be selected from the elective deployment locations, allowing the interventional procedure to be performed from different approaches. The selection of elective deployment locations may also occur during the interventional procedure if the clinician determines that an initially chosen deployment location is unsuitable.

Figure 6:
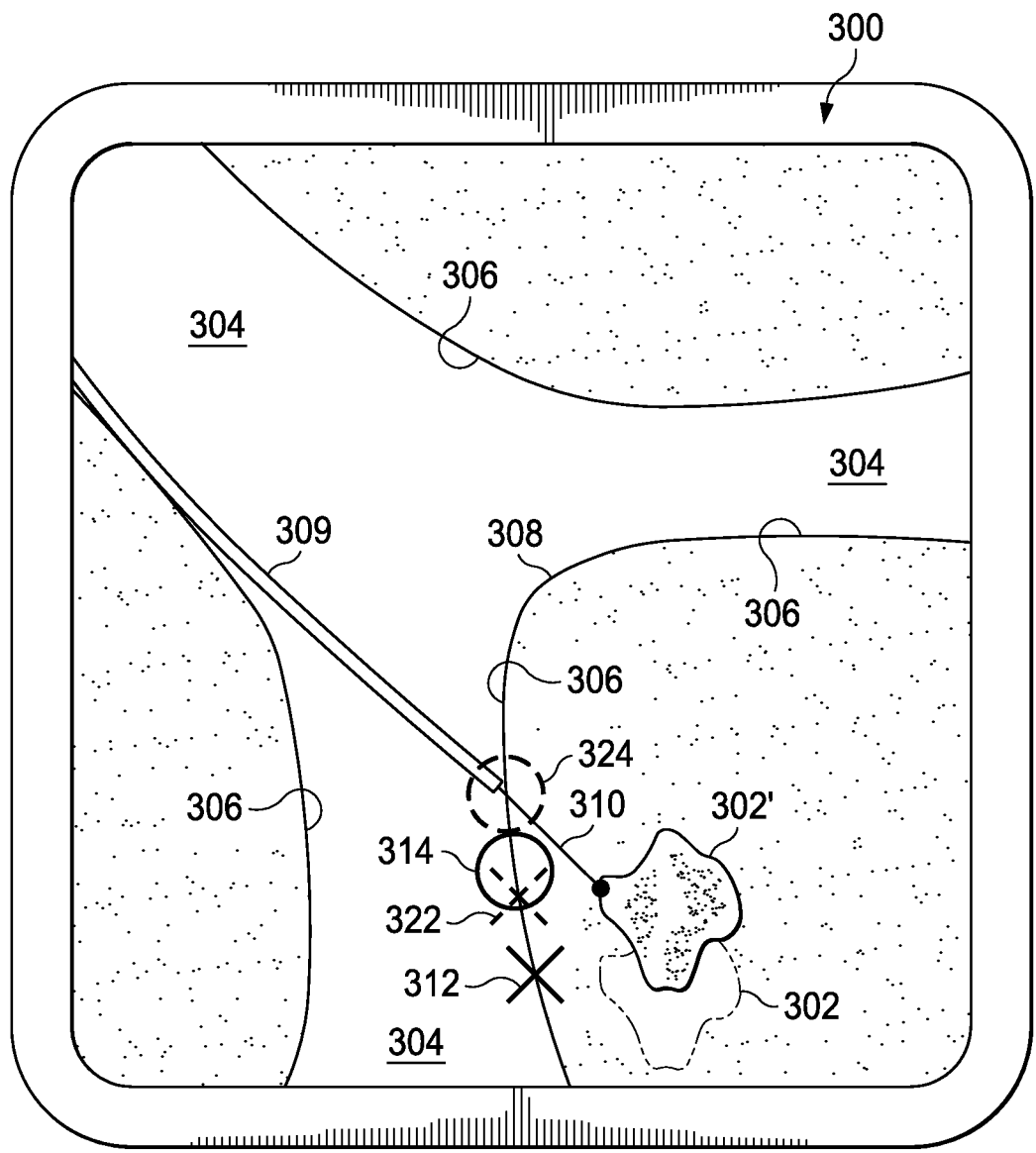
FIG. 6 illustrates an anatomic model image with a distal end of an interventional instrument at a revised deployment location based on sensor feedback.

To further refine the step of identifying the target structure, one or more of the imaging systems 212 may be used to gather additional information about the location of the target structure after the interventional instrument has been deployed to the identified deployment location or the general vicinity thereof. Referring now to FIG. 6, the virtual image 300 of target structure 302 and nearby anatomic passageways 304 is again depicted. The distal end of the flexible body 309 is first positioned at a target confirmation location such as location 312. The image capture probe 226 is operated to determine if the target structure 302 is in the expected position relative to the target confirmation location. If the target structure 302 is not found or not in the expected position, the flexible body and image capture probe can be moved around until the target structure is located. When the target structure is located, the location of the distal end of the flexible body 309 or image capture probe is recorded at a new location 322. The navigation planning module 211 then updates the location of the target structure 302'. With the new location of the target structure identified, the operational capability information for the interventional instrument is used to identify a revised planned deployment location 324. For example, the navigation planning module may use the difference between locations 312 and 322 to update location 314 to location 322 and to update the location of the target structure 302 to 302'. In one embodiment, the image capture probe uses one or more sensors for reflective imaging technology such as ultrasound or OCT to refine the location of the target structure. Alternatively, other non-imaging sensors may be used to identify the location of the target structure.

FIG. 8 is a flowchart describing a method 450 used by the navigation planning module for revising a planned deployment location for an interventional instrument. At 452, information is received from the image capture probe after the probe has been operated at the initial planned deployment location or at a target confirmation location. At 454, a revised location of the target structure is identified using the information received from the image capture probe. At 456, a revised planned deployment location is identified in the model of the plurality of passageways.

Figure 10A:
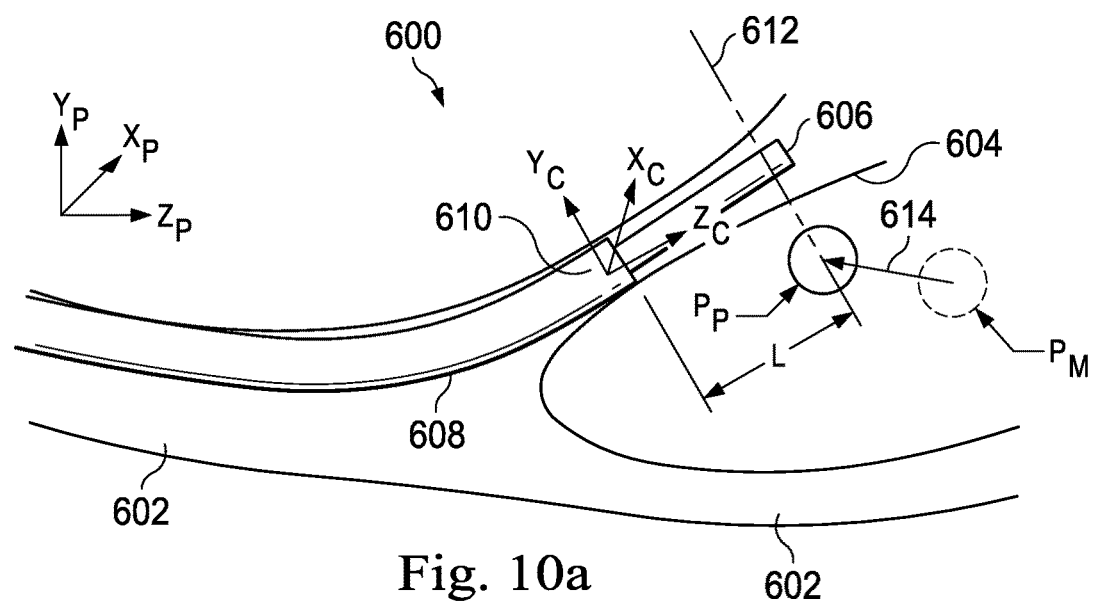
FIG. 10a illustrates an imaging system according to an embodiment of the present disclosure.

The confirmation of the location of the target structure and/or the identification of a revised location of the target structure may be performed using an ultrasound system. The use of ultrasound technology for confirmation and revision of the target structure location may allow for greater accuracy in biopsy or other focal therapies directed to nodules with small diameters (e.g., approximately 10 mm or smaller) FIG. 10a illustrates a virtual image 600 of a target structure $P_M$, such as a tumor, and nearby anatomic passageways 602. The passageways include passageway walls 604. The passageways 602 are located in a patient frame of reference with coordinate system ($X_P$, $Y_P$, $Z_P$). The patient reference frame is a fixed reference frame (i.e., one that does not move during the medical procedure). The image of the plurality of passageways 602 (e.g. obtained from pre- or intra-operative modeling) may be registered to the fixed reference frame. The location of the target structure $P_M$ is determined from pre-operative or intra-operative imaging, as previously described, and is transformed to the patient frame of reference. In this embodiment, the anatomic passageways are bronchial passageways of the lung, but the systems and methods of this disclosure may be suitable for use in other natural or surgically created passageways in anatomical systems such as the colon, the intestines, the kidneys, the heart, or the circulatory system. As previously described, a flexible catheter body 608 (substantially similar to flexible body 216) may be navigated to a catheter park location that allows access to a target structure. The catheter may be navigated using, for example, visual endoscopy, EM sensors, and/or optical fiber shape-based navigation techniques.

An imaging probe 606 is inserted through the flexible catheter body 608. In one embodiment, the imaging probe is an ultrasound probe. The ultrasound probe may be a side-imaging probe including a rotating ultrasound transducer for imaging in a direction generally perpendicular to the axis of rotation of the transducer. The side-imaging probe generates a cross-sectional (i.e., radial) image along an imaging plane 612. A suitable ultrasound probe may be an ultrasonic bronchoscope available from Olympus America, Inc. of Center Valley, Pa. Optionally the ultrasound probe may be integral with the catheter rather than interchangeable as shown in FIG. 10a. In the embodiment of FIG. 10a, the axis of rotation of the transducer is generally along the $Z_C$ direction. A side-imaging probe generates images of the tissue at a radial distance from the axis of rotation, including tissue located outside of the anatomic passageways. In other embodiments, a forward-looking ultrasound probe may be used to image tissue distal of the imaging transducer. The ultrasound probe may be relatively small to navigate narrow anatomical passageways. For example, the ultrasound probe may have distal end diameter of approximately 1.4 mm.

The movement of the probe 606 relative to a distal end portion 610 of the catheter 608 (e.g., the catheter tip) may be tracked. A catheter frame of reference and coordinate system ($X_C$, $Y_C$, $Z_C$) is defined at the distal end portion 610 of the catheter 608 and is registered with the patient coordinate system. The position and orientation of the distal end portion 610 may be tracked, as described above, using sensor systems (e.g., position sensor system 220 and/or the shape sensor system 222) interfaced with a tracking system (e.g., tracking system 206). As the probe 606 is extended from the catheter 608, the position and orientation of the probe may be tracked in the catheter frame of reference and/or in the patient frame of reference. For example, the position and orientation of the probe 606 may be tracked using a positional sensor such as a 5 or 6 degree of freedom EM sensor located on the probe. Alternatively, the movement may be tracked using an insertion sensor such as an encoder located outside the patient anatomy. For example, an encoder associated with a motor that drives the insertion of the probe may be used to determine the insertion length. Alternatively, the movement may be tracked by engaging a stepping motor to control the insertion motion of the imaging probe. A tracked insertion length L is determined between the distal end portion 610 of the catheter and the imaging plane 612 of the probe (e.g., the image plane of the side-imaging ultrasound transducer)

Figure 10B:
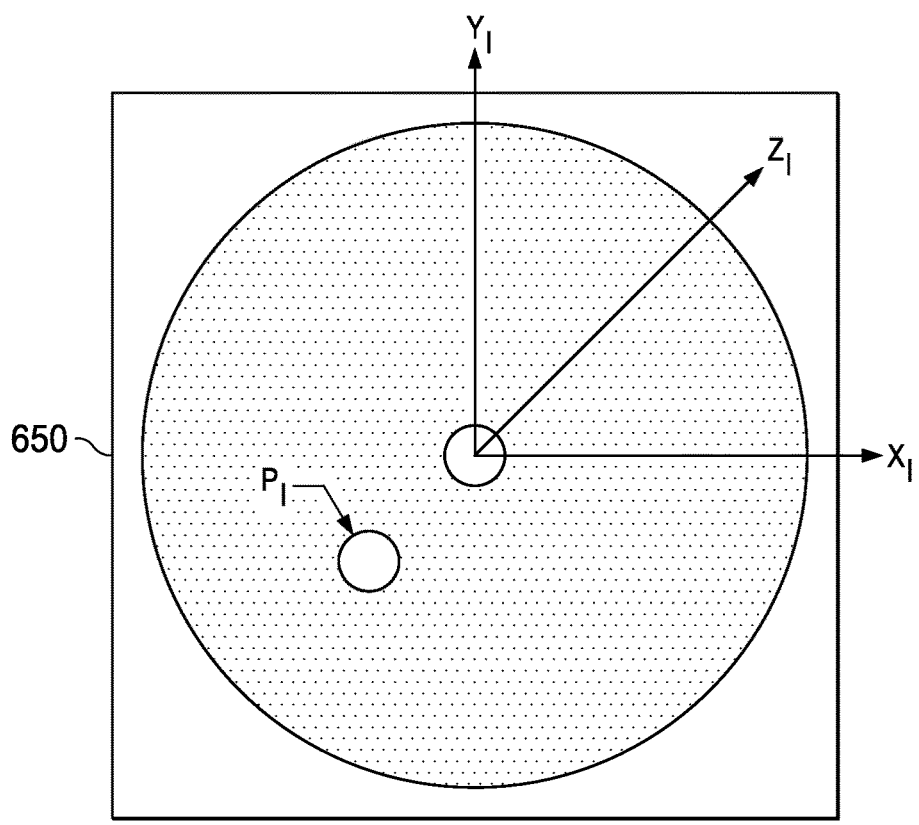

FIG. 10b illustrates an image 650 generated by the ultrasound probe 606 in the imaging plane 612 shown in FIG. 10a. The image 650 has an image frame of reference and coordinate system ($X_I$, $Y_I$, $Z_I$). The target structure $P_I$ is identified in the image frame of reference. It may be identified, for example, by a clinician, by an image analysis algorithm, or by a combination of the two. The ultrasound scan may be gated for respiratory and/or cardiac cycles. Although the image 650 is two-dimensional, a three-dimensional image may be constructed from a plurality of two-dimensional ultrasound scans. Data associated with the location of the target structure $P_I$ in the image frame of reference is transformed to the catheter coordinate system or the patient coordinate system (that has been registered with the catheter coordinate system) as $P_P$. The location of the target structure $P_P$ as determined by the ultrasound probe may be compared to the location of the target structure $P_M$ determined from pre-operative or intra-operative imaging in the catheter or patient frame of reference to determine a correction vector 614. The correction vector 614 is the offset value between the location of the target structure $P_M$ and the location of the target structure $P_P$.

Figure 11:
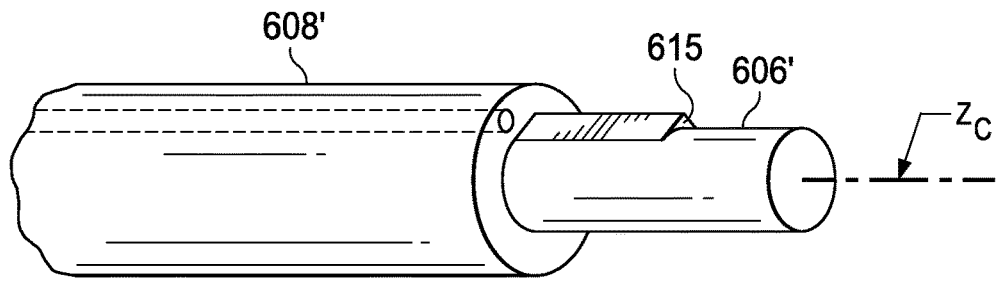
FIG. 11 illustrates an alternative embodiment of an imaging system according to an embodiment of the present disclosure.

To transform the image coordinate system to the catheter coordinate system, the relative three-dimensional pose between the image coordinate system and the catheter coordinate system is determined. It can be measured directly by sensors on the catheter and imaging probe. Such sensors may include an EM sensor, a fiber optic shape sensor, or the like. The sensors on the catheter and the imaging probe do not need to be of the same type. The relative three-dimensional pose may also be determined by two or more images of the catheter using, for example, fluoroscopy. In case the full three-dimensional pose is not directly measured, the same information can be computed by measuring the insertion length L and a known roll angle of the image coordinate system with respect to the catheter coordinate system, assuming the imaging probe extends straight beyond the tip of the catheter and the pose of the catheter end is known. The insertion length L may be determined using, for example, an encoder, a stepping motor, or external imaging (e.g., fluoroscopy). The roll angle may be determined using a variety of techniques. In one embodiment, as shown in FIG. 11, an ultrasound probe 606' includes a roll alignment feature 615 keyed to the catheter 608'. The roll alignment feature 615 causes the probe 606 to maintain a fixed orientation about the catheter roll axis (Zc) extending through the catheter. The roll alignment feature allows the roll angle of the image reference frame of reference and coordinate system ($X_I$, $Y_I$, $Z_I$) to be registered with respect to the catheter reference frame and coordinate system ($X_C$, $Y_C$, $Z_C$). In this embodiment, the roll alignment feature is a shaped protrusion keyed to match a similarly shaped channel in the catheter. In alternative embodiments, the roll alignment feature may be a channel shaped to match a protrusion in the catheter. More than one roll alignment feature may be used to maintain the probe in a fixed orientation about the catheter roll axis. In various other embodiments, the roll angle of the image coordinate system with respect to the catheter coordinate system may be determined by a roll sensor located outside of the patient anatomy may be used. In still another alternative, the roll angle may be determined by viewing one or more markers or other features with a known angle relative to the catheter in the image recorded by the imaging probe. For example, the feature or marker may be located on the circumference of the catheter and have a contrast (e.g. an ultrasound contrast) to the catheter. In another alternative, the combined roll and insertion length may be determined by observing a pattern on the probe around the proximal end of the catheter or by observing a pattern on the catheter around the proximal end of the probe.

Figure 12:
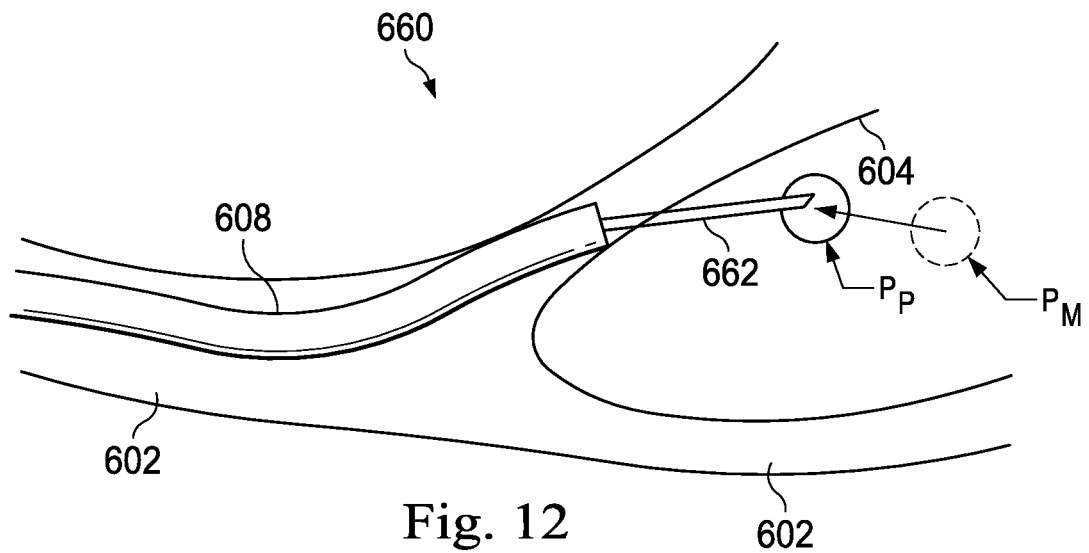
FIG. 12 illustrates a biopsy procedure according to an embodiment of the present disclosure.

After the ultrasound probe 606 is removed from the catheter 608 and replaced with a biopsy instrument 662. As shown in FIG. 12, the catheter 608 may be steered to a revised position and/or orientation that provides access to the revised target location $P_P$. The steering of the catheter may be accomplished directly by active steering control of the catheter or indirectly by navigating a steerable biopsy instrument 662. The biopsy instrument 662 is extended from the catheter 608, through the wall 604 of the anatomic passageway 602 and into contact with the tumor structure located at revised target location $P_P$.

Figure 9:
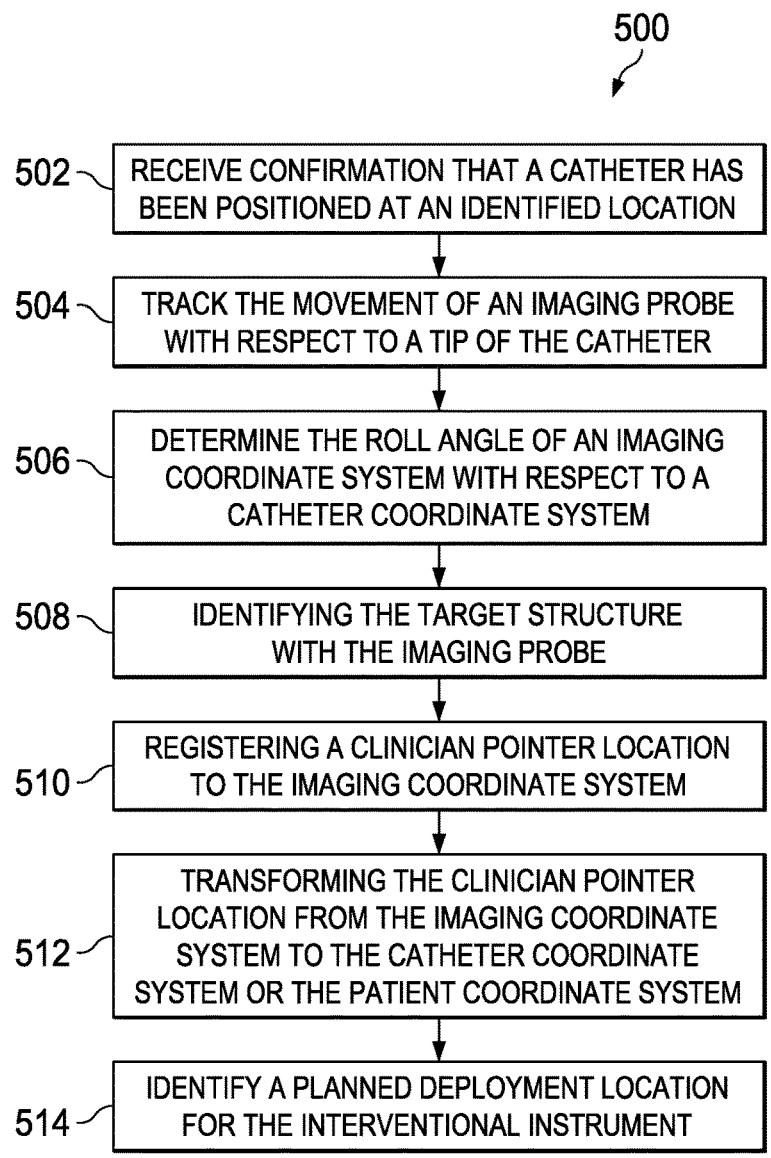
FIG. 9 is a flowchart describing a method for identifying the target structure using the imaging systems.

A method 500 for identifying the target structure using the ultrasound probe 606 is described at FIG. 9. The method 500 may be performed to identify an initial interventional deployment location or may be used to identify a revised deployment location as described below.

At 502, the catheter 608 is navigated to a passageway location (e.g., location 312 or 314) with the guidance of the navigation system including, for example, visual, EM or shape sensor information. A confirmation from the clinician or from the interventional instrument may be provided when the catheter has reached the location. At 504, the probe 606 is inserted through the catheter 608 and the movement (i.e. insertion length) of the probe relative to the distal end portion 610 of the catheter is tracked. In some embodiments, the same probe 606 may also be used in performing the navigation to the passageway location at step 502. The movement of the probe 606 may be tracked, for example using a positional sensor such as a 5 or 6 degree of freedom EM sensor. Alternatively, the movement may be tracked using an insertion sensor such as an encoder located outside the patient anatomy. Alternatively, the movement may be tracked by engaging a stepping motor to control the insertion motion of the imaging probe.

At 506, a roll angle of the image coordinate system ($X_I$, $Y_I$, $Z_I$) is determined with respect to the catheter frame of reference and coordinate system ($X_c$, $Y_c$, $Z_c$). For example, the roll angle may be determined using the roll alignment feature of the imaging probe and the catheter. Alternatively, a roll sensor located outside of the patient anatomy may be used. In still another alternative, the roll angle may be determined by viewing one or more markers or other features with a known angle relative to the catheter in the image recorded by the imaging probe. For example, the feature or marker may be located on the circumference of the catheter and have a contrast (e.g. an ultrasound contrast) to the catheter. Alternatively, the roll angle and the insertion length of the imaging probe with respect to the catheter may be measured by an optical sensor (e.g., a camera) that is fixed to the catheter observing a visual pattern placed around the imaging probe. The visual pattern may contain features that uniquely determine two-dimensional locations. Examples of such patterns may be found in U.S. Pat. No. 8,223,193, filed Mar. 30, 2009, disclosing "Targets, Fixtures, and Workflows for Calibrating an Endoscopic Camera," which is incorporated by reference herein in its entirety.

Figure 13A:
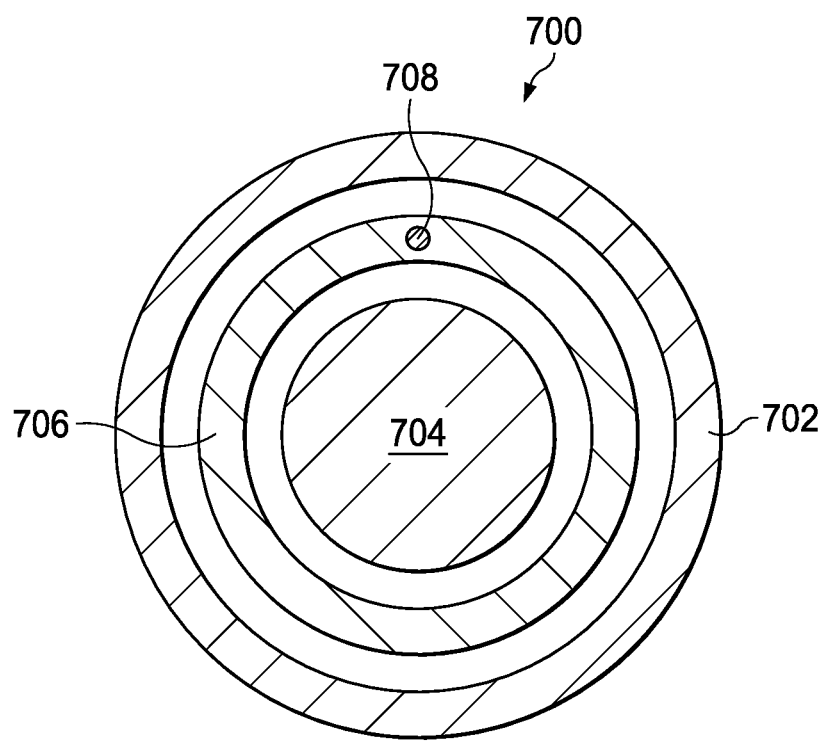
FIGS. 13a and 13c illustrate cross-sectional views of an ultrasound imaging probe according to another embodiment of the present disclosure.
Figure 13B:
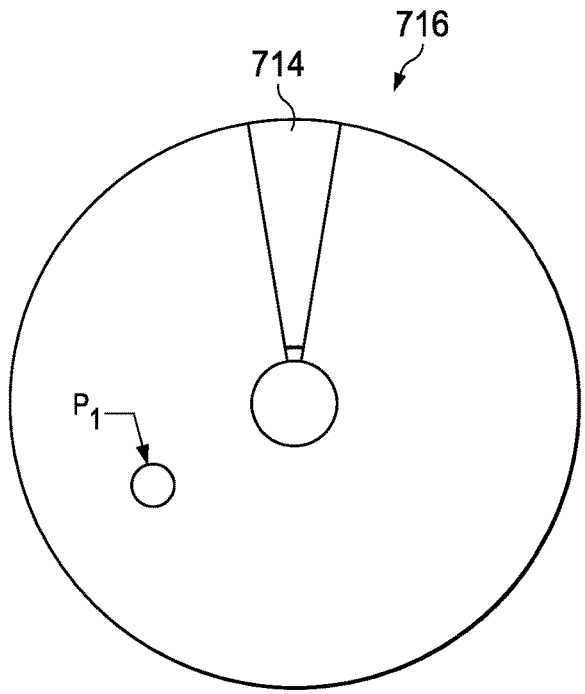
FIG. 13b illustrates an image from the ultrasound imaging probe of FIGS. 13a and 13c.
Figure 13C:
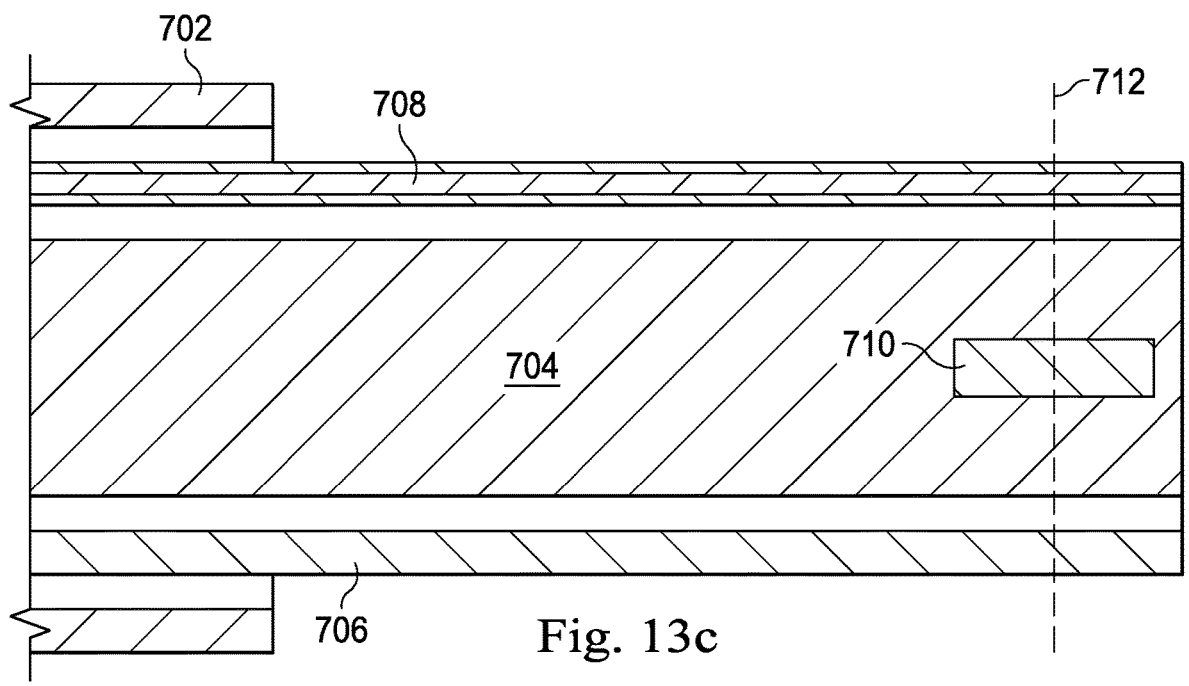

In an alternative embodiment as shown in FIGS. 13a-c, a mechanically rotating radial ultrasound probe assembly 700 provides an indicator to reference roll angle. Assembly 700 includes a catheter 702 through which extends an ultrasound probe 704 surrounded at least in part by a sheath 706. The sheath 706 is rotatably fixed (e.g. may be keyed) relative to the catheter 702. An ultrasound opaque marker 708 is located on the sheath 706 within an area through which the acoustic energy from the transducer 710 of ultrasound probe 704 passes to create an image plane 712. In this embodiment, the sheath 706 that is transparent to ultrasound except for the marker 708 on a circumferential area of the sheath cross-section. The marker section that blocks ultrasound creates an identifiable contrast region 714 in the ultrasound image 716 so that it can be used as a reference roll angle. The body of the sheath 706 can be constructed using a material that has acoustic impedance that matches the ultrasound probe and the tissue so that the acoustic energy can pass the sheath with little loss. The alignment mark 708 may be constructed using a material that has significantly different acoustic impedance to that of the ultrasound probe and the tissue so that it reflects most of the reflective energy to the transducer 710.

In various other embodiments, the ultrasound probe (particularly the tip where the transducer is located) may be tracked because the ultrasound probe may not extend distally straight from the catheter. For example, a fiber optic shape sensor (as described above) may be used to track the location of the ultrasound probe tip. The shape sensor may be incorporated into the ultrasound probe or into a sheath surrounding the probe. Additionally or alternatively, one or more fluoroscopy images may be used to determine the position of the tip of the ultrasound probe. Additionally or alternatively, an EM sensor may be used to track the tip of the ultrasound probe.

At 508, the catheter 608 and/or the probe 606 are moved, in response to teleoperational, manual, or computer operated control, within the anatomic passageways to locate the target structure for display in an image generated by the probe. More specifically, ultrasound images may be generated by the ultrasound probe within the passageways. The ultrasound images allow a clinician to visualize the area within the passageway and areas of tissue outside of the passageways, immediately adjacent to and surrounding the passageway. The ultrasound images also allow a clinician to visualize tissue, including target tissue, located further away from the wall of the passageway, for example, at a radial distance of up to a few centimeters from the central axis of the probe, depending upon the type of tissue being imaged.

At 510, after the target structure is detected by the probe 606, a clinician may identify the target structure in the image using a pointing device. The image (e.g. the ultrasound image) may be generated by a scan that is gated for respiratory and/or cardiac cycles. A three-dimensional image may be constructed from two-dimensional scans. The location identified by the pointing device is identified and recorded as the pointer location data. At 512, the pointer location data is transformed from the image coordinate system ($X_I$, $Y_I$, $Z_I$) to the catheter coordinate system ($X_C$, $Y_C$, $Z_C$) or to the patient coordinate system ($X_P$, $Y_P$, $Z_P$) (which has been previously registered to the catheter coordinate system).

At 514, the pointer location data can be used to apply an offset correction (e.g., the offset correction vector 614) to the location of the target structure identified initially in the preoperative anatomic model. A revised target structure location (e.g., revised target location $P_P$) is computed based upon the offset correction vector. The revised target location may be in the catheter coordinate system and/or the patient coordinate system. This revised target structure location may then be displayed to the clinician in an image with the patient anatomical passageways and/or the catheter. The probe 606 may then be removed from the catheter 608. A biopsy tool or other interventional tool (e.g., instrument 662) may be inserted through the catheter to perform a focal procedure (e.g., a biopsy) at the revised target location. Optionally, the probe 606 may be reinserted through the catheter 608 after the interventional procedure. The reinserted probe may conduct a scan and produce images for clinician review to confirm whether the biopsied tissue was, in fact, the target tissue.

As described above, the probe 606 may be used for target tissue confirmation and correction. In alternative embodiments, the probe 606 and catheter 608 may be used to conduct the initial navigation to the initial target location based on the pre-operative images. In still other alternative embodiments, the probe 606 and catheter 608 may be used for post-biopsy confirmation. Because a lung passageway is generally filled with air rather than fluid or tissue the effectiveness of ultrasound imaging may be somewhat limited for longer-distance navigation purposes. Ultrasound imaging may thus be particularly effective for location confirmation/correction or for post-biopsy confirmation.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method of deploying an interventional instrument, the method performed by a processing system, the method comprising:
   registering a distal segment of a guide catheter with a patient coordinate system;
   tracking, using a tracking system, a position of the distal segment of the guide catheter;
   determining an insertion length between an imaging probe and the distal segment of the guide catheter based on the tracked position of the distal segment of the guide catheter, wherein the imaging probe is extendably disposed within the guide catheter;
   with the imaging probe extended to the insertion length relative to the distal segment of the guide catheter, receiving an image of an anatomic structure from the imaging probe, the image having an image frame of reference, the distal segment of the guide catheter having a catheter frame of reference;
   receiving location data associated with a target structure identified in the image, wherein the received location data is in the image frame of reference; and
   transforming the location data associated with the target structure from the image frame of reference to the catheter frame of reference based on the determined insertion length and the tracked position of the distal segment of the guide catheter, wherein transforming the location data associated with the target structure from the image frame of reference to the catheter frame of reference further includes determining a roll angle for the image frame of reference with respect to the catheter frame of reference.

2. The method of claim 1 further comprising:
   registering the catheter frame of reference to a patient frame of reference; and
   transforming the location data associated with the target structure from the catheter frame of reference to the patient frame of reference.

3. The method of claim 1 further comprising:
   receiving location data associated with the target structure identified in a patient model; and
   determining an offset correction vector between the location data associated with the target structure identified in the image and the location data associated with the target structure identified in the patient model.

4. The method of claim 3 further comprising:
   generating an image of the patient model with an image of the target structure adjusted based upon the offset correction vector.

5. The method of claim 1 wherein determining the insertion length includes receiving position indication data from an electromagnetic sensor.

6. The method of claim 1 wherein determining the insertion length includes receiving position indication data from an encoder located outside a patient anatomy.

7. The method of claim 1 wherein determining the insertion length includes monitoring motion of a stepping motor.

8. The method of claim 1 wherein determining the roll angle for the image frame of reference with respect to the catheter frame of reference includes interfacing a roll alignment feature of the imaging probe with the guide catheter.

9. The method of claim 1 wherein determining the roll angle for the image frame of reference with respect to the catheter frame of reference includes obtaining the roll angle from a roll sensor located outside of a patient anatomy.

10. The method of claim 1 wherein determining the roll angle for the image frame of reference with respect to the catheter frame of reference includes detecting a feature having a known angle with respect to the guide catheter in the image.

11. The method of claim 1 wherein determining the roll angle for the image frame of reference with respect to the catheter frame of reference includes locating a contrast region in the image, wherein the contrast region is caused by a feature on the guide catheter.

12. The method of claim 1 wherein the imaging probe is an ultrasound imaging probe.

13. A system comprising:
   non-transitory computer readable media containing computer executable instructions for planning a procedure to deploy an interventional instrument including:
   instructions for registering a distal segment of a guide catheter with a patient coordinate system;
   instructions for tracking, using a tracking system, a position of the distal segment of the guide catheter;

instructions for determining an insertion length between an imaging probe and the distal segment of the guide catheter based on the tracked position of the distal segment of the guide catheter, wherein the imaging probe is extendably disposed within the guide catheter;

instructions for receiving an image of an anatomic structure from the imaging probe while extended the insertion length beyond the distal segment of the guide catheter, the image having an image frame of reference, the distal segment of the guide catheter having a catheter frame of reference;

instructions for receiving location data associated with a target structure identified in the image, wherein the received location data is in the image frame of reference; and instructions for transforming the location data associated with the target structure from the image frame of reference to the catheter frame of reference based on the insertion length and the tracked position of the distal segment of the guide catheter, wherein transforming the location data associated with the target structure from the image frame of reference to the catheter frame of reference further includes determining a roll angle for the image frame of reference with respect to the catheter frame of reference.

14. The system of claim 13 further comprising:
the guide catheter.

15. The system of claim 13 further comprising:
the imaging probe.

16. The system of claim 13 wherein the non-transitory computer readable media contains computer executable instructions for planning the procedure to deploy the interventional instrument further including:
instructions for registering the catheter frame of reference to a patient frame of reference; and
instructions for transforming the location data associated with the target structure from the catheter frame of reference to the patient frame of reference.

17. The system of claim 13 wherein the non-transitory computer readable media contains computer executable instructions for planning the procedure to deploy the interventional instrument further including:
instructions for receiving location data associated with the target structure identified in a patient model; and
instructions for determining an offset correction vector between the location data associated with the target structure identified in the image and the location data associated with the target structure identified in the patient model.

18. The system of claim 17 wherein the non-transitory computer readable media contains computer executable instructions for planning the procedure to deploy the interventional instrument further including:
instructions for displaying an image of the patient model with an image of the target structure adjusted based upon the offset correction vector.

19. The system of claim 13 wherein the insertion length is from a distal end of the guide catheter to a plane of the image received from the imaging probe.

20. The system of claim 19 wherein the instructions for determining the insertion length include instructions for receiving position indication data from an electromagnetic sensor on the imaging probe.

21. The system of claim 19 wherein the instructions for determining the insertion length include instructions for receiving position indication data from an encoder located outside a patient anatomy.

22. The system of claim 19 wherein the instructions for determining the insertion length include instructions for monitoring motion of a stepping motor.

23. The system of claim 13 wherein the instructions for determining the roll angle for the image frame of reference with respect to the catheter frame of reference include instructions for interfacing a roll alignment feature of the imaging probe with the guide catheter.

24. The system of claim 13 wherein the instructions for determining the roll angle for the image frame of reference with respect to the catheter frame of reference include instructions for obtaining the roll angle from a roll sensor located outside of a patient anatomy.

25. The system of claim 13 wherein the instructions for determining the roll angle for the image frame of reference with respect to the catheter frame of reference include instructions for detecting a feature having a known angle with respect to the guide catheter in the image.

26. The system of claim 13 wherein the imaging probe is an ultrasound imaging probe.

27. The method of claim 1 further comprising:
determining a location of the target structure relative to the distal segment of the guide catheter based on the location data in the catheter frame of reference.

* * * * *